United States Patent
Robergs et al.

(10) Patent No.: US 6,942,623 B2
(45) Date of Patent: Sep. 13, 2005

(54) MIXING CHAMBER AND EXPIRED GAS SAMPLING FOR EXPIRED GAS ANALYSIS INDIRECT CALORIMETRY

(75) Inventors: Robert A. Robergs, Tijeras, NM (US); Joseph Weir, Mitchellville, IA (US)

(73) Assignee: Science & Technology@ UNM, Albuquerque, NM (US)

( * ) Notice: Subject to any disclaimer, the term of this patent is extended or adjusted under 35 U.S.C. 154(b) by 38 days.

(21) Appl. No.: 10/382,149

(22) Filed: Mar. 5, 2003

(65) Prior Publication Data

US 2004/0176698 A1 Sep. 9, 2004

(51) Int. Cl.[7] .................................................. A61B 5/08
(52) U.S. Cl. ...................................... 600/531; 600/532
(58) Field of Search ................................ 600/529, 531, 600/532, 533, 538, 537, 540, 541, 543; 128/200.24

(56) References Cited

U.S. PATENT DOCUMENTS

| | | | |
|---|---|---|---|
| 4,292,978 A | * 10/1981 | Guth ........................... | 600/543 |
| 4,572,208 A | * 2/1986 | Cutler et al. ................. | 600/531 |
| 4,619,269 A | 10/1986 | Cutler et al. | |
| 5,363,857 A | 11/1994 | Howard | |
| 5,584,285 A | * 12/1996 | Salter et al. ........... | 128/200.21 |
| 5,720,277 A | 2/1998 | Olsson et al. | |
| 6,277,645 B1 | 8/2001 | Mault | |
| 6,325,978 B1 | 12/2001 | Labuda et al. | |
| 6,406,435 B1 | 6/2002 | Mault | |
| 6,468,222 B1 | * 10/2002 | Mault et al. ................. | 600/531 |
| 6,475,158 B1 | 11/2002 | Orr et al. | |

FOREIGN PATENT DOCUMENTS

WO     WO 9205738 A1 * 4/1992 ........... A61B/5/097

* cited by examiner

*Primary Examiner*—Mary Beth Jones
*Assistant Examiner*—Navin Natnithithadha
(74) *Attorney, Agent, or Firm*—Dorsey & Whitney LLP

(57) ABSTRACT

There is provided an improved system for expired gas analysis indirect analysis indirect calorimetry comprising a unique compliant mixing chamber that is directly connected to a mouthpiece that, itself, is unique in providing enhanced saliva and expired moisture trapping capability. The volume of the inspired and expired gas as well as at least the oxygen and carbon dioxide concentrations in the expired gas in the mixing chamber are determined. The metabolic rate of the subject is calculated therefrom taking into account the anatomical dead space in the body of the subject. The mixing chamber is compliant, sized to accommodate a single expiration and partially open to the environment. Preferably, the system also includes means to determine the oxygen and carbon dioxide content of the inspired gas as well.

20 Claims, 2 Drawing Sheets

MIXING CHAMBER AND EXPIRED GAS SAMPLING FOR EXPIRED GAS ANALYSIS INDIRECT CALORIMETRY

FIELD OF THE INVENTION

The present invention relates to a system for gas analysis of a subject's expiration. More particularly, the present invention relates to an improved system for the gas analysis of expiration that provides enhanced accuracy over present systems.

BACKGROUND OF THE INVENTION

The measurement of metabolism or metabolic rate has application in a varied number of fields including exercise physiology, biology, physiology, biochemistry, nutrition, fitness, cardiology, pulmonology, endocrinology and physical therapy. Such measurements find utility in physiological measures, e.g. as part of routine physical examinations, as adjuncts to medical treatments and monitoring functions relating to a variety of conditions related to the heart, respiratory system, obesity and others. Such measurements are also widely used in conjunction with sports and general fitness programs.

The most common method of carrying out such determinations is by indirect calorimetry. This is a non-invasive means of determining the body's metabolic activity through oxygen consumption and carbon dioxide production. The method, fundamentally, entails measurement of ventilation, sampling the subject's inhalation and exhalation and determining the oxygen and carbon dioxide content of each. These measurements can be used to quantify the body's energy expenditure and metabolic state, and may also be utilized to detect certain disease processes such as, for example, obstructive lung disease, heart disease and peripheral vascular disease.

There are a number of systems available to carry out the determination of the oxygen/carbon dioxide in exhaled air. These vary in complexity, principle of operation and design. The most basic of these is the Douglas bag, which has been in use for about fifty years. This is a static system which consists of a large, flexible bag having a capacity typically from about fifty to as much as two hundred liters. The Douglas bag can be used as a rebreathing apparatus that is well suited for such measurements as lung profusion. In this measurement, the subject continuously inhales a mixture of air and a radioactive gas from the bag so that lung morphology and functioning may be studied with specialized equipment by monitoring the movement of the radioactive gas in the lungs. However, a static system, such as the Douglas bag, is not well suited for the collection of exhaled air, as for continuous indirect calorimetry, partially because of its volume and partially due to the length of time required, usually from about thirty seconds to one minute, for the collection of a sufficient volume of expired air. This is true even with more modem sensors and other similar improvements to the basic Douglas bag apparatus.

There are a number of systems available that have the capacity to measure and compute data from samples taken of exhaled air at given intervals of time, e.g. 15 seconds, 30 seconds, 60 seconds, or each breath. For the breath-by-breath systems, the oxygen and carbon dioxide content of samples of the exhaled gas stream is determined and compared to the inhaled gas mixture to establish a curve. These systems are potentially flawed, however, because during exercise when the frequency of breathing increases significantly, the breath-average curves developed from these measurements can become distorted with resultant loss of accuracy. The time-averaged systems suffer the disadvantage of having the results skewed due to the associated dead air space in the system consisting of tubing directing air to a constant volume chamber where it is mixed. This dead air space, in combination with the typical size of the fixed volume mixing chamber, typically one to five liters, act to decrease the overall sensitivity and accuracy of the system.

Another factor that is often discounted, but which can also distort results of indirect calorimetry, even on sophisticated equipment, is the anatomical dead space (ADS) in the body which results in alveolar air being present during inhalation, and atmospheric air during exhalation. While it is not difficult to determine the ADS volume, it has largely been ignored due to the misconception that its effect is negligible and/or that it is adequately counteracted by or compensated for by the atmospheric air in the ADS during exhalation. We have found, however, that the effect of the ADS does not appear to be self-correcting and results in appreciable errors in the determination of the volume of exhaled oxygen and carbon dioxide.

In addition to the aforementioned factors that contribute to inaccuracies in determinations of indirect calorimetry utilizing known systems, the configuration of systems in use may also contribute to variations in the results obtained. The size and efficiency of the mixing chamber, its proximity to the mouthpiece, the locus of the sampling device and the construction of the mouthpiece itself are all factors that may contribute to inaccuracies in indirect calorimetry measures. It will be appreciated that the impact of any one of these factors on the accuracy of the results will in large part be dependent on the purpose of the determination. Further, where more than one of these factors is at work in a given system, the overall detrimental effect will be even more pronounced. There are situations where accuracy is critical to determinations, such as the calculation of the dosage of certain medications, where the margin for error must be as small as possible. It will be appreciated that, the more critical the need for accuracy, the greater the impact of these factors. In accordance with the present invention, there is provided a system for indirect calorimetry that minimizes or eliminates the disadvantages of known systems as described above.

SUMMARY OF THE INVENTION

The system of the present invention comprises a unique mixing chamber that is operably connected directly to a mouthpiece, wherein the mouthpiece has ports for inhalation and expiration, each including a turbine or other one-way valve. The system includes means to determine the volume of gas that enters and exits the mouthpiece and means to withdraw a sample of at least the expired gas in the mixing chamber, preferably both the expired gas and the inhalation gas source, and determine the oxygen and carbon dioxide content thereof. The analyses are provided to a suitable computer means that transposes the various determinations into desired data. The determinations by the computer means are programmed to include the anatomical dead space in the respiratory system of the subject breathing into the system. Both the mixing chamber and the mouthpiece have unique aspects that are advantageous to the operation and accuracy of the system.

BRIEF DESCRIPTION OF THE DRAWINGS

Further objects and advantages of the present invention will be more fully appreciated from a reading of the detailed description when considered with the accompanying drawings wherein.

DETAILED DESCRIPTION OF THE INVENTION

Figure 1:
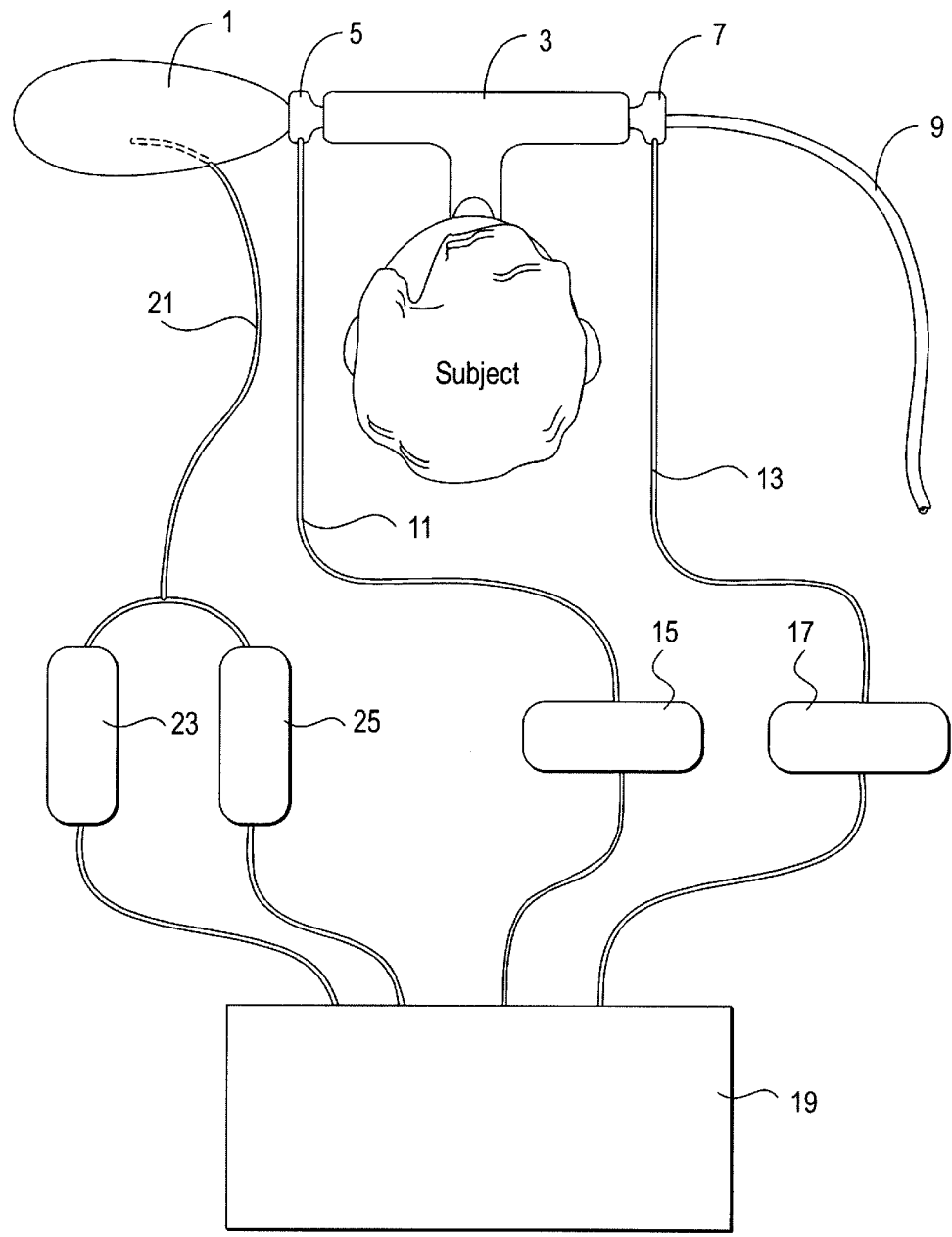
FIG. 1 is a diagram of a system for indirect calorimetry in accordance with the present invention.

The measurement system of the present invention is comprised of a unique compliant mixing chamber in direct operable communication with a mouthpiece that has unique features and which includes a suitable one-way valve, such as a turbine, on both the inhalation and exhalation portals. The system includes means to determine the volume of gas entering and exiting the mouthpiece and means to analyze the oxygen and carbon dioxide content of at least the expired gas in the mixing chamber. Preferably, the system further includes means to analyze the oxygen and carbon dioxide content of the gas to be inspired as well. The system further includes computer means that has the capacity to receive data from the various determinations and generate analyses and comparisons of the oxygen and carbon dioxide content of both inhalation and expiration and, thereby, the metabolic rate of the subject, specifically taking into account the Anatomical Dead Space (ADS) as discussed above. Such computer means are known to those of ordinary skill in the art and are commercially available. Suitable analytical computer means are standard equipment in hospitals as well as diagnostic testing facilities and many physical care facilities.

The software required to operate such computer means is likewise known to those of ordinary skill in the art. However, the difference in the system according to the present invention is the correction for the ADS that has heretofore been believed to have negligible effect or have been adequately counteracted by the atmospheric air in the ADS during exhalation. The effect that calculating the ADS into the determinations realized by the use of the present system can be seen from the following. Traditionally, calculations for indirect calorimetry utilize the Haldane transformation which requires measurement of only one of $V_I$ or $V_E$ as follows:

$$V_I * F_1 N_2 = V_E * F_E N_2$$

$$V_I = (V_E * F_E N_2) F_1 N_2$$

$$= (V_E * [1-(F_E O_2 + F_E CO_2)])/0.7903$$

wherein $V_I$ and $V_E$ are the volume of inhalation and exhalation, respectively, $F_I$ and $F_E$ are the fractions sampled from inhalation and exhalation, respectively, $N_2$ is nitrogen and the symbol * represents multiplication. As shown in Table I below, analyses based on such traditional computations are flawed in comparison to analyses based on the computations of the system of the present invention including calculation for ADS.

TABLE I

| Measurement | Traditional Calculation | With ADS |
|---|---|---|
| $F_I O_2$ | 0.2093 | 0.2055 |
| $F_I CO_2$ | 0.0003 | 0.0036 |
| $F_E O_2$ | 0.1684 | 0.1693 |
| $F_E CO_2$ | 0.0452 | 0.0455 |
| $VO_2$ | 4.99 | 4.52 |
| $VCO_2$ | 5.64 | 5.23 |
| RER | 1.13 | 1.16 |

In the above calculations, RER is the ratio between production of carbon dioxide and consumption of oxygen. It can be seen from the data presented in Table I that the failure to calculate for the ADS does have a significant effect on the accuracy of the measurement.

The essence of the basis for the measurement of the present invention is that the average expired gas fraction is altered by: the ADS volume and the gas fraction; the volume of expired lung air and expired lung gas fraction; and the expired volume of air. These relationships are detailed in the following equation:

$$F_E O_2 = ((VE * F_E O_2) - (ADS * 0.2093))/(VE - ADS)$$

The above and tabled calculations were based on a single condition wherein $V_1=125$ L/min. and ADS=0.15 L. As the fraction of total ventilation that is alveolar increases, the error in failing to adjust for ADS air decreases. Therefore, the error would be greater during rest and low exercise conditions and decreases progressively as exercise intensity increases. Regardless, the error is still meaningful as shown above, even for a high exercise intensity wherein the errors for $VO_2$ and $VCO_2$ are 10.4% and 7.8%, respectively. Overall, the error in not accounting for ADS causes overestimations of $VO_2$ and $VCO_2$ and a slight underestimation of RER.

It will be appreciated by those skilled in the respective arts that the impact of such errors in measurement will be directly related to the condition of the subject and the reason for taking the measurement. It will also be appreciated that, although typically not taken into consideration, the measurement and calculation of ADS is within the purview of one of ordinary skill in the art. Since the calculations to determine ADS and the computer means required to analyze the readings from the sensor means are within the skill of the art, they will not be discussed further herein except to note that they are included within the system of the present invention.

The mixing chamber in accordance with the system of the present invention is a compliant vessel that has a capacity such that it will accommodate a full exhalation. For an adult, this will typically be approximately three liters, although larger mixing containers may be used when the subject is an adult undergoing strenuous exercise. Small mixing chambers may be used as well when the subjects are children. In general, therefore, the mixing chamber will have a capacity of from about one to five liters, preferably about three liters. This is significantly less than a conventional Douglas Bag that typically has a capacity of from about fifty to two hundred liters. Unlike a Douglas Bag, however, the mixing chamber of the present invention is a flow-through vessel that is partially open to the environment. Therefore, the mixing chamber will accommodate a full exhalation by virtue of its compliance and, at the end of the exhalation, will recoil to force some of the exhalation out until a point of pressure equalization is reached where the pressure gradient within the bag prevents atmospheric air from entering and there is insufficient pressure within the bag to force further exhalation out.

The configuration and location of the vent apertures in the mixing chamber is not critical to the operation thereof so long as there is sufficient flow from the mixing chamber to permit at least about 50%, preferably about 90% of the contents to flow out at the end of exhalation before pressure equalizing stabilizes flow in and out. In general, the walls of the mixing chamber will not recoil with a force that will expel all of its contents. While this is certainly possible, it is considered of greater importance that the walls of the mixing chamber are sufficiently compliant to accommodate the exhalation. The mixing chamber may be constructed of any suitable material that has sufficient compliance to provide for it to expand with the pressure of a typical exhalation, i.e. from about 1 to 5 cm $H_2O$. Such materials are known to those of ordinary skill in the art and the use of a particular material is not critical to the practice of the system of the invention. Suitable materials include thin plastic, rubber, latex and rubber latex blends. A preferred material is latex or a latex/rubber blend.

In the system of the present invention, the mixing chamber as described above is operably connected directly to the mouthpiece utilized by the subject. A typical system of the present invention is illustrated in FIG. 1. The compliant mixing chamber 1 is operably connected to the mouthpiece 3 via a suitable one-way valve connection, such as a turbine 5. A similar one-way valve 7 connects the mouthpiece 3 to the tubing 9 that introduces air for inspiration into the mouthpiece 3. The system of the present invention as illustrated in FIG. 1 includes tubing 9 which would ordinarily be utilized only when the subject was inhaling a particular blend of gases, most commonly oxygen-enriched air. When the subject is to breath atmospheric air, tubing 9 would not be required and would not be present in the subject system. Means to determine the volume of gas entering and exiting the mouthpiece 3 are shown in sensor lines 11 and 13 from the one-way valves 5 and 7, respectively, that are connected via flow modules 15 and 17, respectively, to a computer 19 that has the capability to receive information from all sensors and provide the desired data and calculations as discussed above. A sample of the exhalation in the mixing chamber 1 is provided via line 21 to oxygen and carbon dioxide analyzers, 23 and 25 that, in turn, submit data on the oxygen and carbon dioxide content thereof to the computer 19. Preferably, if the air to be inspired is not premixed to an exact oxygen concentration and introduced through a closed system, a sample of the air to be inspired is obtained by a suitable device, not shown, and passed through a line, also not shown, to the oxygen and carbon dioxide analyzers 23 and 25, or to a separate pair of analyzers, not shown, and the resultant data submitted to the computer 19.

Figure 2:
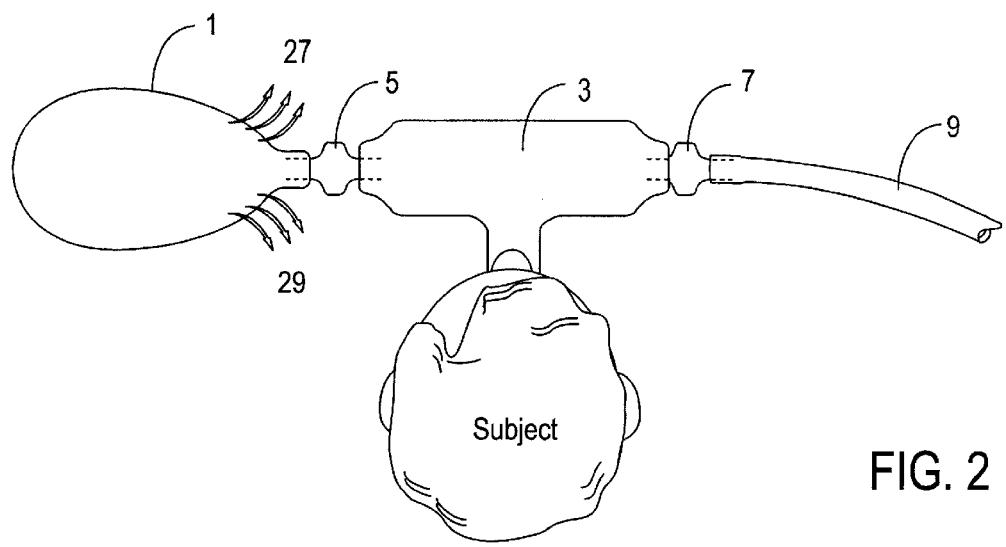
FIG. 2 is diagram illustrating the configuration of the mixing chamber and mouthpiece of the system shown in FIG. 1.

In FIG. 2, there is illustrated a detailed view of the operable connections among the mixing chamber 1, the mouthpiece 3 and the inspiration tube 9. This view illustrates a preferred embodiment of mixing chamber 1 wherein air flow of the exhalation is discharged from the area proximate to the connection to the one-way valve 5 at the end of exhalation. While this is a preferred configuration, those of ordinary skill in the art will recognize that there are other configurations that will accomplish the same purpose. Such other configurations are considered to be within the purview of the present invention. The apertures in mixing chamber 1 may be of any desired size shape and orientation, the only requirement being that they permit at least about 50%, preferably up to 90%, of the exhalation within the mixing chamber to flow from the mixing chamber in the direction of the arrows 27 at the end of exhalation as the mixing chamber recoils.

In operation, the subject inhales thereby drawing air from the tube 9, or directly from the environment when a special blend of gases in not utilized, through the one-way valve or turbine 7. The volume of inhalation through one-way valve 7 is determined via sensor line 13 and flow module 17. At the end of inhalation, the subject exhales, thereby closing one-way valve 7 and opening one-way valve 5 to emit the exhalation into the mixing chamber 1. The volume flow through one-way valve 5 is measured via sensor line 11 and flow module 15, and the information provided to the computer 19. As the exhalation enters the compliant mixing chamber 1, it expands thereby promoting through mixing of the exhalation. It has been found in accordance with the present invention that the sample fraction is preferably taken in the subject system between breaths as this is the time when the gas composition in the mixing chamber 1 is most indicative of the gas composition expired by the lungs. A convenient means of accomplishing this is to cause the closing of one-way valve 5 at the end of the expiration phase to trigger activation of the sampling in the mixing chamber 1. By this means, the sample will be taken at relatively the same point in the breathing cycle regardless of how rapidly the subject is breathing.

As mixing chamber 1 is reaching maximum expansion, some of the exhalation is already beginning to flow out in the direction of flow 27. As the exhalation weakens toward the end of the phase, the mixing chamber 1 begins to recoil, thus forcing more exhalation therefrom until a state of equilibrium is established where no further exhalation flows from the chamber, yet there remains sufficient pressure within that atmospheric air cannot enter. The mixing chamber 1 is then ready to repeat the cycle. As previously indicated, the inspiration tube 9 may contain, and preferably does contain, sampling means to provide the computer means 19 with data on the composition of the air being inhaled.

It has been found in accordance with the present invention that the direct connection of the mixing chamber 1 to the mouthpiece 3 is advantageous over the conventional use of tubing as a conduit from a mouthpiece to a sampling device and/or a mixing chamber. We have found that both proximity to the mouthpiece and a small, compliant mixing chamber improve the sensitivity of the measurements taken by the present system. The conventional use of tubing is disadvantageous for two reasons. First, because it is typically from one to three meters in length, it significantly delays the response time of the system by the time required for the exhalation to travel through the tubing and reach the sampling or analyzing device. The effect of this delay becomes more significant as the breathing rate of the subject increases. It will be appreciated that the diameter of the tubing is also a factor since gas will flow more rapidly through a narrow tubing than a wide tubing of the same length. However, the tubing cannot be too small since the smaller the diameter, the greater the resistance to flow and the greater work required to move the exhaled air through the tubing. Regardless of the diameter and length of the tubing, the dead exhaled air remaining in the tubing is the second disadvantage since it must be factored into the analytical determination to be provided by the system In a similar manner, we have found that the difference in volume of two mixing chambers constructed of similar material can have an impact on the sensitivity of the measurement. For example, under similar test conditions where other factors are relatively constant, decreasing the size of a mixing chamber from 2.5 liters to one liter resulted in an improvement in relative sensitivity of measurement of nearly three fold. It can be seen, therefore, that the advantages of the unique mixing chamber of the present invention are the result of its size, its high compliance and low to moderate elasticity, and the fact that it is operably connected directly to the mouthpiece, thereby eliminating any tubing that would detract from the overall sensitivity of the system as described above.

Figure 3A:
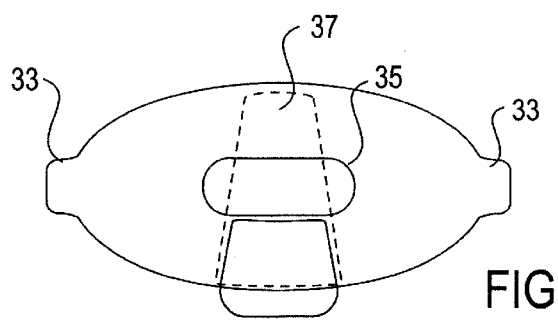
FIGS. 3a and 3b are front and side views, respectively, of the unique mouthpiece of the system of the present invention.
Figure 3B:
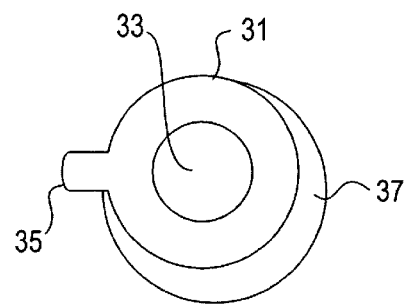

The system of the present invention is further characterized by an improved mouthpiece. As shown in FIGS. 3A and 3B, the mouthpiece of the invention has an ovoid body 31 having apertures at the ends 33 suitable for connection to one-way valves 5, turbines or other similar devices. The apertures may have projections, as illustrated, or may have any other art-recognized structures by which the one-way valves 5 and 7 may be attached, e.g. an opening that would form a substantially air-tight fit with a one-way valve that includes a projection of the appropriate size and configuration. The mouthpiece has a retainer projection 35 that is retained in the mouth of the subject. This projection may be any desired shape, but is also preferably ovoid for comfort to the user. The projection may be removable for disposal, or may be of such construction that a removable confirming sleeve, not shown, may be fitted over it and discarded after each use. Preferably, the mouthpiece assembly is constructed of materials suitable for disposal such that it may be disengaged and replaced after each use.

Mouthpieces utilized on breathing systems such as described herein typically include a narrow tube at the bottom for expired moisture and saliva to collect and flow downward out of the mouthpiece. This structure is effective only when the subject positions his or her head such that the tube is essentially in a vertical alignment. Otherwise, saliva and expired moisture will collect in the expired region of the mouthpiece, and eventually may be forced from within the mouthpiece into the flow turbine and expired tubing. The result can be a negative impact on the functioning of the one-way valve on the expired side as well as introducing error into the measurement taken by the system. The mouthpiece of the system of the present invention is advantageous over such conventional mouthpieces in that it contains an enlarged depression to collect and retain saliva and expired water vapor.

Referring again to FIGS. 3A and 3B, the mouthpiece of the system of the present invention is characterized by a saliva trap 37 that extends from the retainer projection 35 from about 50% to about 75%, preferably from about 65% to about 67% of the circumference of the mouthpiece 31 in a direction perpendicular to a line bisecting the two ends 33. It will be appreciated that it is not necessary for the saliva trap 37 to extend beyond 75% of the circumference of the mouthpiece 31 because, in use, the mouthpiece will be held such that the ends 33 are approximately parallel to the floor. Hence, it will be held such that the saliva trap 37 extends from the retainer projection 35 in a downward direction. Having an elongated retainer projection 35 assures that this will occur.

Saliva trap 37 is preferably a trough that has approximately parallel sides which converge to a point over approximately 10% of its length at either end. The width of saliva trap 37 is from about 10% to about 50%, preferably about 20% of the width of the mouthpiece. The depth of the saliva trap 37 is from about 1 to 3 cm, preferably about 1 cm. from the inner surface of the mouthpiece 31. A preferable saliva trap 37 would extend from the retainer projection 35 approximately 66% of the circumference of a mouthpiece 31 and at its widest point, be approximately 20% of the width of the mouthpiece 31 and be approximately 1 cm in depth from the inner surface of the mouthpiece 31. The exact shape of the saliva trap 37 is not particularly critical to the practice of the invention so long as it generally conforms to the parameters set forth herein.

The saliva trap 37 is advantageous in that it encompasses approximately two-thirds of the circumference of the mouthpiece 31 thereby permitting the subject's head to be in different positions without sacrifice of its effectiveness. The saliva trap 37 is further advantageous in that it is large enough to accommodate a strip of suitable absorbent material, such as gauze or paper towel, that will retain fluid and promote the efficiency thereof. Such a strip may be provided with the mouthpiece 31 in the instance of a disposable unit, or may be inserted by the user at the time of use. The mouthpiece of the subject system is advantageous for the reasons stated, more comfortable for the subject, and as a result of reducing the possibility of saliva and moisture contaminating the expiration valve and affecting the measurements, an asset to the overall accuracy and reliability of the system.

The expired gas analysis indirect calorimetry system in accordance with the present invention provides enhanced accuracy and reliability. The system may be utilized to sample expiration at specified intervals or between each breath. The system may be adapted to sampling under a variety of conditions and has the capacity for enhanced accuracy under even rapid breathing as when the subject is undergoing exercise. A particular advantage of the system of the present invention is that it does not suffer a material loss in sensitivity of measurement from changes in the metabolism of the subject. The unique compliant mixing chamber of the subject system that is connected directly to the expired side of the mouthpiece, in combination with including ADS as a factor in the determinations, gives a more accurate analysis with a minimum of dead air space. The unique mouthpiece further enhances the overall efficacy of the system by providing improved capacity to trap saliva and expired moisture during use. The fact that the unique mouthpiece of the subject system permits movement of the subject's head is particularly advantageous for measurements to be taken when the subject is undergoing exercise.

It should be understood that various changes and modifications to the preferred embodiments will be apparent to those skilled in the art. Such changes and modifications can be made without departing from the spirit and scope of this invention and without diminishing its attendant advantages. It is therefore intended that such changes and modifications be covered by the appended claims

What is claimed is:

1. A system for expired gas analysis indirect calorimetry comprising:

a) a compliant mixing chamber having a capacity such that will accommodate a full exhalation and being partially vented to the environment;

b) a mouthpiece having separate one-way valve means to permit the flow of gas to be inspired therein and the flow of expired gas therefrom, the mouthpiece being operably directly connected to the compliant mixing chamber via said one-way valve means permitting the flow of expired gas therefrom;

c) means to determine the volume of gas entering and exiting said mouthpiece;

d) means to analyze the oxygen and carbon dioxide content of the expired gas from said compliant mixing chamber thereof; and e) computer means to calculate the metabolic rate of a subject breathing into said mouthpiece based on said determination and analysis, wherein the anatomical dead space in the breathing system of said subject is included in said calculation.

2. A system is accordance with claim 1, wherein said compliant mixing chamber has a capacity of from approximately one to five liters.

3. A system is accordance with claim 2, wherein said compliant mixing chamber has a capacity of approximately three liters.

4. A system in accordance with claim 3, wherein said means to analyze the oxygen and carbon dioxide content of the gas to be inspired includes a device to obtain a sample of the air to be inspired.

5. A system in accordance with claim 1 further including means to analyze the oxygen and carbon dioxide content of the gas to be inspired.

6. A system in accordance with claim 1, wherein said system is programmed to calculate the metabolic rate of the subject after each breath.

7. A system in accordance with claim 1, wherein said mouthpiece is constructed of suitable material such that it may be replaced after each use.

8. A system in accordance with claim 1, wherein the venting of said mixing chamber is such that at least about 50% of the expired gas will be vented at the end of exhalation.

9. A system in accordance with claim 8, wherein about 90% of the expired gas will be vented at the end of exhalation.

10. A system in accordance with claim 1, wherein said means to analyze the oxygen and carbon dioxide content of the expired gas includes a device to withdraw a sample of the expired air from the compliant mixing chamber.

11. A system in accordance with claim 1, wherein said system determines the metabolic rate of a subject between breaths.

12. A system in accordance with claim 1, wherein said mouthpiece has an ovoid body having a saliva trap extending from said retainer projection from about 50% to about 75% of the circumference of said body in a direction perpendicular to a line bisecting said ends, said saliva trap being from about 10% to about 50% of the width of said body at its widest point and from about 1 to about 3 cm in depth from the inner surface of the body.

13. A system in accordance with claim 12, wherein said saliva trap contains material having the capacity to absorb saliva and expired moisture.

14. A system in accordance with claim 12, wherein said saliva trap extends from said retainer projection from about 66% of the circumference of said body and said saliva trap is about 50% of the width of said body at its widest point.

15. A mouthpiece for a breathing apparatus comprising an ovoid body having apertures at the ends thereof for gas to enter and exit, respectively, and a retainer projection to be retained by a subject breathing therethrough, said mouthpiece having a saliva trap extending from said retainer projection from about 50% to about 75% of the circumference of said body in a direction perpendicular to a line bisecting said ends, said saliva trap being from about 10% to about 50% of the width of said body at its widest point and from about 1 to about 3 cm in depth from the inner surface of the body.

16. A mouthpiece in accordance with claim 15, wherein said mouthpiece includes one-way valve means situated in said apertures to permit the flow of gas to be inspired therein and the flow of expired gas therefrom.

17. A mouthpiece in accordance with claim 15, wherein said saliva trap contains material having the capacity to absorb saliva and expired moisture.

18. A mouthpiece in accordance with claim 15, wherein said saliva trap extends from said retainer projection from about 66% of the circumference of said body.

19. A mouthpiece in accordance with claim 15, wherein said saliva trap is about 50% of the width of said body at its widest point.

20. A mouthpiece in accordance with claim 15, wherein said mouthpiece is in the shape of an elongated trough and has a depth of about 1 cm from the inner surface of said body.

* * * * *